United States Patent
Carrieri et al.

(10) Patent No.: US 7,262,414 B1
(45) Date of Patent: Aug. 28, 2007

(54) THERMAL LUMINESCENCE SURFACE CONTAMINATION DETECTION SYSTEM

(75) Inventors: Arthur H. Carrieri, Abingdon, MD (US); Erik S. Roese, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 11/208,128

(22) Filed: Aug. 17, 2005

(51) Int. Cl.
G01N 21/35 (2006.01)
G01N 21/63 (2006.01)

(52) U.S. Cl. ................................ 250/341.6; 250/339.08
(58) Field of Classification Search ........... 250/339.08, 250/341.6
See application file for complete search history.

(56) References Cited

U.S. PATENT DOCUMENTS

| 5,241,179 A | 8/1993 | Carrieri |
| 5,631,469 A | 5/1997 | Carrieri et al. |
| 6,464,392 B1 | 10/2002 | Carrieri et al. |
| 6,731,804 B1 | 5/2004 | Carrieri et al. |

FOREIGN PATENT DOCUMENTS

JP 05303961 A * 11/1993

* cited by examiner

*Primary Examiner*—Constantine Hannaher
(74) *Attorney, Agent, or Firm*—Ulysses John Biffoni

(57) ABSTRACT

A Thermal Luminescent (TL) spectroscopy system and method for remote sensing and detection of surface chemical contamination involves irradiation of a target surface with energy from a near infrared pump beam, and measurement of TL liberated by that surface within a middle infrared (MIR) region. Fundamental molecular vibration modes of target contaminants present are briefly activated after the surface has been driven out of thermal equilibrium. An emissivity contrast between strata and target contaminant develops, peaks, and then subsides during a finite thermal window of detection opportunity in which detection of fingerprint identifiers for target contaminants is most probable. Target contaminant identification employs neural network models trained and tested against known molecular absorption frequencies of target contaminants. The use of a pump beam that radiates energy outside the MIR spectra of received TL reduces possible interference with the very weak MIR signals given off by target contaminants.

19 Claims, 7 Drawing Sheets

THERMAL LUMINESCENCE SURFACE CONTAMINATION DETECTION SYSTEM

GOVERNMENT INTEREST

The invention described herein may be manufactured, licensed, and used by or for the U.S. Government.

TECHNICAL FIELD

The present invention relates in general to a system and method for detecting chemical and biological materials at a distance. More particularly, the present invention identifies target contaminants, such as liquid chemical warfare agents, or simulants of such compounds, and other infrared absorbing substances on a surface at a distance by recognizing the substances' infrared fingerprint or signature spectrum brought out in thermal luminescence (TL) spectroscopy.

BACKGROUND

A variety of systems and methods have been developed and used to detect and identify hazardous chemical and biological threat agents in the field. Chemical test kits that employ chemically reactive vapor-samplers and detection papers have long been used to detect chemical nerve agents, blood agents, and blister agents. While chemical kits are useful, they are designed to detect a limited range of conventional chemical agents that are toxic in the range of $10^{-3}$ g/person, provide no standoff protection and may be prone to false negative and positive detections.

Systems that employ Ion Mobility Spectrometry (IMS) in which molecules are ionized and separated according to their differences in velocities through a gas in the presence of an electric field can, in theory, identify and detect a wide variety of chemical and biological warfare (CBW) agents. IMS systems, however, require direct exposure to the chemical agent and the instruments typically have insufficient resolving power to identify CBW agents before they have reached casualty producing levels.

Other systems employ passive infrared (PIR) imaging to detect airborne chemical threats such as nerve (GA, GB, and GD) and blister (H and L) agents based on the infrared spectrum of the agent. Currently fielded devices have been reported to detect aerosols at a distance of up to 5 km. Practical PIR detection systems have difficulty detecting low levels of CBW surface target contaminants because the surfaces are typically at thermal equilibrium and provide insufficient contrast to identify target contaminants. Additionally, background radiation and interference encountered in the field can also make detection difficult.

What is needed is a system and method for use in the field that rapidly, reliably, and repeatably detects the presence or absence of a wide variety of surface target contaminants at very low levels and can be operated remotely at a safe distance in order to detect target contaminants before casualty producing concentrations are encountered. Embodiments according to the present invention address these needs, at least in part.

The following patents are incorporated herein by reference for background purposes as if fully set forth: U.S. Pat. No. 6,731,804, issued May 4, 2004 to Carrieri, et al; U.S. Pat. No. 5,241,179, issued Aug. 31, 1993 to Carrieri; U.S. Pat. No. 6,464,392, issued Oct. 15, 2002 to Carrieri, et al.; and U.S. Pat. No. 5,631,469 issued May 20, 1997 to Carrieri, et al.

SUMMARY

A TL spectroscopy system and method for remote sensing and detection of surface liquid chemical contamination are disclosed. In one aspect, a system for remote sensing and detection of surface chemical target contaminants according to the present invention includes a near infrared source to irradiate the surface and excite an emission of middle infrared thermal luminescence, a middle infrared sensor to detect the emission of middle infrared thermal luminescence, a scanning interferometer to process the detected middle infrared TL by introducing streaming waveform outputs, a processor to transform the streaming waveform outputs into spectra, a processor to identify surface thermal gradient peaks, a processor to identify emissivity contrasts between stratum and target contaminant to define a thermal window in which target contaminant signature spectra are likely to be found, a database comprising target contaminant signature spectra to develop a model, and an algorithm to compare a model of target contaminant signature spectra with middle infrared spectra in the thermal window to detect and identify target contaminants.

In another aspect, a method for detecting target contaminants according to the present invention includes irradiating a surface with a near infrared energy source to induce a thermal gradient, scanning the surface interferometrically to detect middle-infrared emissions, windowing detected middle infrared emissions to capture data substantially centered on a thermal gradient peak, and processing the data to extract molecular vibration bands that can be employed to identify target contaminants. In another aspect, a neural network model trained against known molecular absorption frequencies of target contaminants is employed to extract the molecular vibration bands that can be employed to identify target contaminants. In still another aspect, a minimum near infrared energy source irradiation time [0 $\tau_{min}$] to maximize thermal luminescent flux as the surface is driven into thermal non-equilibrium is estimated by performing a numerical optimization on one or more irradiating beam source parameters. The optimization may include a genetic algorithm that operates on the one or more irradiating beam source parameters in order to arrive at a thermally dynamic state of the surface in minimum τ, i.e., $\partial^2 \mathcal{R}/\partial \tau^2|_{\tau=\tau_{min}}=0$.

Other aspects, features, and advantages of the present invention will become apparent to those skilled in the art from the detailed description and the accompanying drawings. It should be understood, however, that the detailed description and accompanying drawings, while indicating preferred embodiments of the present invention, are given by way of illustration and not of limitation. Many changes and modifications may be made within the scope of the present invention without departing from the spirit thereof, and the invention includes all such modifications.

DETAILED DESCRIPTION

Figure 1:
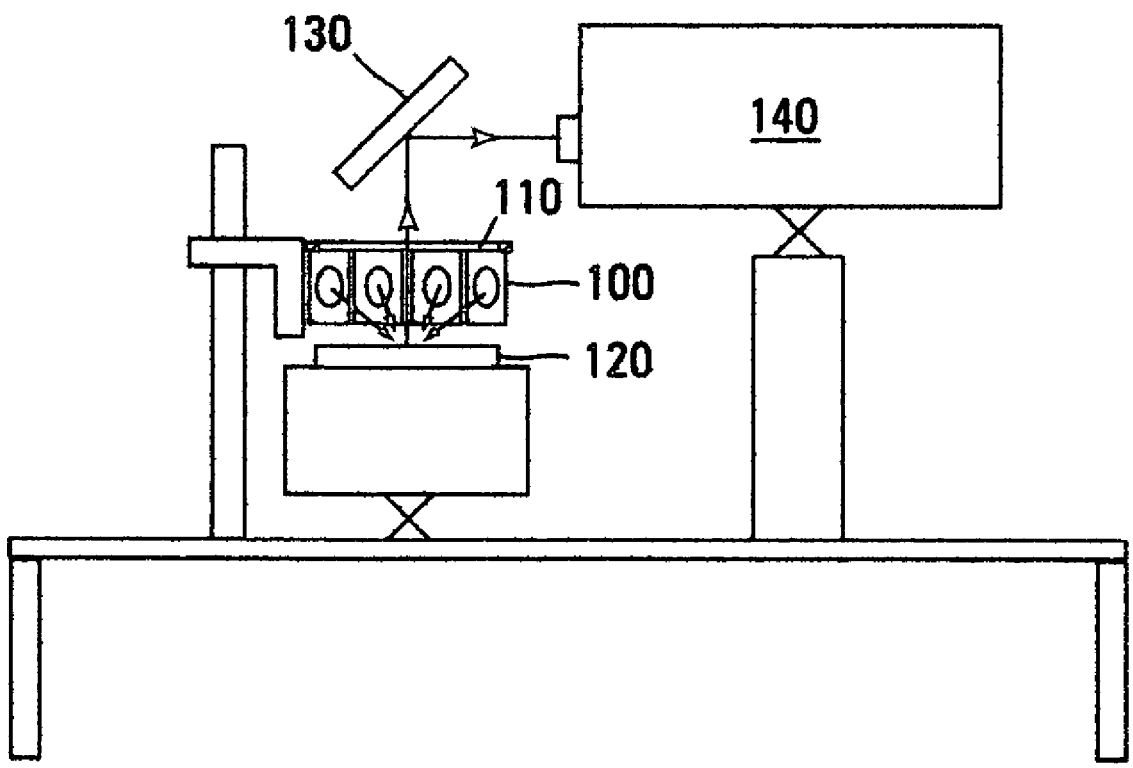
FIG. 1 shows a schematic diagram of an embodiment of a TL surface contamination detection system according to the present invention.

In the following detailed description, reference is made to the accompanying drawings which form a part hereof, and in which are shown by way of illustration specific embodiments in which the invention, as claimed, may be practiced. This invention may, however, be embodied in many different forms and should not be construed as limited to the embodiments set forth; rather, these embodiments are provided so that this disclosure will be thorough and complete, and will fully convey the scope of the invention to those skilled in the art. As will be appreciated by those of skill in the art, the present invention may be embodied in methods, systems, and devices. Wherever possible, the same reference numbers will be used throughout the drawings to refer to the same or like parts.

Thermal luminescence (TL), as the term is used herein, refers to a near IR radiation-induced excitation of an atomic system, such as a molecule, that results in the emission of a middle infrared (MIR) radiance. This liberated radiance may be used to identify the molecular structure of the atomic system. In particular, vibrational spectra that uniquely identify molecular structures of substantially all surface target contaminants, i.e., the so-called "fingerprint" "signature" or characteristic spectra of the contaminants, are known to resonate in the MIR band.

MIR radiance including the characteristic vibrational spectra of any target contaminants can be excited by irradiating a surface with an energy source. The energy source can lie within the excitation bandwidth, or outside the excitation bandwidth. In particular, a near IR beam can be used to excite vibrational spectra in the MR band. Vibrational spectra of surface target contaminants can be derived from a terrestrial surface comprising a substrate and one or more layers of liquid driven out of temperature equilibrium. To resolve these exceedingly weak spectra, an emissivity contrast can be built between the substrate and liquid target contaminant layers, as a consequence of continuing beam irradiance. Contrast building at discrete molecular resonance energies of target contaminants contained in the middle-infrared band of luminescent flux is of particular significance. This building emissivity contrast provides a well defined thermal window of detection opportunity; i.e., some finite irradiation timeframe in which fingerprint spectra of target contaminants are enhanced and much more likely to be identified.

The surface is probed by directing a near infrared beam over the area while liberated middle infrared emissions are measured via a scanning interferometer. A remote controlled robotic unit may be used to scan potentially contaminated surfaces from a safe distance. The beam, which can be derived from a source that is coherent or incoherent, pulsed or continuous, provides sufficient intensity in the NIR band to excite a detectable MIR dynamic surface heat flux or gradient from the surface area of interest. The MIR emissions are processed by the interferometer into streaming waveform outputs or interferograms which are transformed into spectra by conventional signal processing techniques such as grouping, co-adding, averaging, and the like. While the irradiation continues, the spectra are processed to identify surface thermal gradient peaks. For example, the spectra may be subtracted in contiguous order during the developing thermal gradient event. These spectra that are a manifestation of the surface in its most thermally dynamic state, i.e., when thermal gradient peaks during irradiation, are examined to identify emissivity contrasts between stratum and target contaminant. Detection is positive when an absorption or emission band profile unique to a target contaminant mass is resolved in the difference spectra metric.

TL is derived from the inelastic energy coupling between an incident beam and a material such as a terrestrial or any inhomogeneous dielectric surface. Transfer of electromagnetic field energy from beam to surface material is governed by absorption cross-section quantities $\sigma_\lambda$, where $\lambda$ ranges over the beam's energy band and is very narrow (generally broad) for coherent (incoherent) sources. Furthermore, heat transportation as driven by the irradiating beam is governed by thermal conductivity $\kappa$ of material. Another manifestation of irradiation is the uniform generation of heat flux above the irradiation zone, which is functionally related to $\sigma_\lambda$ and $\kappa$. The specific 6.67–16.67 μm MIR band of this liberated radiance (also referred to as 1500-600 cm$^{-1}$ wave numbers or reciprocal wavelength) is where TL is found. During irradiation, liberated emissions reach maximum flux output and subside as the medium attains thermal equilibrium at elevated temperature. Surface temperature gradients develop and then collapse to a skin depth of beam penetration, for irradiated dielectrics. These dynamic developments of thermal gradient, which occur in phase with energy coupling ($\sigma$) and internal heat conduction ($\kappa$) mechanisms, are captured when substrate and target contaminant are at maximum emissivity contrast—a state of material in which TL flux output is also maximum. It is within this windowed timeframe of maximum gradient development that absorption of TL by the interstitial target contaminant is most pronounced. Herein, certain molecular species are excited to natural modes of vibration resonance that are fundamental, i.e., primary, atom groups of molecules are in active resonance. This radiometric signal translates to, and is superimposed on the TL emissions envelope of irradiated material (good absorbers are good emitters). The detection task concerns resolving frequencies and strengths of TL absorption by the target contaminant molecules (small radiance) superimposed onto the total liberated emissions field (dominant radiance).

In general, a near IR excitation source should be selected to generate the dynamic thermal surface glow, or TL, necessary for detection of interstitial target contaminant mass. For example, a tungsten-halogen (WBr$_2$) lamp with emissions output that peak in intensity at about 1.10 μm and decrease to near zero intensity at 4.57 μm is likely to be adequate for most terrain and man-made landscapes that possess high absorption cross-sections in the 6.67-16.67 μm region (600-1500 cm$^{-1}$ wave-numbers/reciprocal wavelengths). A variety of other near IR, MIR, and far IR sources may be used depending on the requirements of a particular application.

The resulting TL that has been liberated by the near-infrared-irradiance of the surface is scanned interferometrically, Fourier-transformed into spectra, and subtracted sequentially in a finite timeframe substantially concurrent to irradiation. The fingerprint identifier of a target contaminant is then searched for in this difference-spectra field. By applying statistical physics methods to the randomly rough substrate-target contaminant layer, with appropriate boundary conditions, the physical mechanism driving TL can be modeled in a thermal diffusion partial differential equation. Initial and final conditions are ambient surface temperature just before beam irradiation and steady-state temperature attained after continuing exposure from the constant-intensity beam, respectively. Numerical expressions are solvable that define intrinsic temperature gain of the surface during irradiation, relating material properties ($\sigma_\lambda$, thermal conductivities $\kappa$, specific heats $C_p$, mass densities $\rho$, and statistical heights $<h>$ and slopes $<\delta>$ of target contaminant-substrate) to the source term (excitation beam of duration [$\tau$], intensity [I], wavelength [$\lambda$] and polarization [Stokes vector, S]). The thermal gradient is evaluated as it develops between target contaminant and substrate layers during irradiation, and, from this, the radiant TL flux output ($\partial \mathcal{R} \partial \tau$) from the irradiation zone is computed.

The minimum beam irradiation timeframe [0, $\tau_{min}$] required to maximize thermal luminescent flux (as the surface is driven into thermal non-equilibrium) can be estimated by performing an optimization on the source beam parameters. Optimization may be facilitated through integration of a genetic algorithm (GA) into the TL model equations, tag pump beam variables $\lambda$, I, and S, and by performing an iterative global search on those parameters toward this GA goal, seeking the most thermally dynamic state of surface in minimum $\tau$, i.e. $\partial^2 \mathcal{R} \partial \tau^2|_{\tau=\tau_{min}}=0$. The foregoing procedure facilitates design of a high performance detection system, including NIR source, TL sensor and signal processing apparatus, optimized for collection of data for target contaminant and substrate in a state of peak emissivity contrast; i.e., about the $\tau_{min}$ neighborhood.

A weak signature radiance of a target contaminant, i.e., its frequencies and amplitudes of molecular vibration resonance, will be superimposed onto the dynamic surface TL envelop (approximately 100× target contaminant spectral signal strength), if present. Hence, TL carries the minute spectrum signal of a surrogate contaminant, in situ, as described next.

As alluded to earlier, heat transportation as driven by the irradiating beam is governed by thermal conductivity $\kappa$ of material. Another manifestation of irradiation is the uniform generation of heat flux above the irradiation zone, which is functionally related to $\sigma_\lambda$ and $\kappa$. The specific 6.67-16.67 µm (1500-600 cm$^{-1}$ wave numbers or reciprocal wavelength) MIR band of this liberated radiance is what we call TL. During irradiation, liberated emissions reach maximum flux output and subside as the medium attains thermal equilibrium at elevated temperature. Surface temperature gradients will develop then collapse to a skin depth of beam penetration, for irradiated dielectrics. These dynamic developments of thermal gradient, which occur in phase with energy coupling ($\alpha$) and internal heat conduction ($\kappa$) mechanisms, are captured when substrate and target contaminant are at maximum emissivity contrast $\sigma_\lambda$ a state of material in which TL flux output is also maximum. It is within this windowed timeframe of maximum gradient development that absorption of TL by the interstitial target contaminant is most pronounced. Herein, certain molecular species will excite into natural modes of vibration resonance that are fundamental, i.e., the primary, atom groups of molecules are in active resonance. This radiometric signal translates to, and is superimposed on, the TL emissions envelope of irradiated material (i.e., good absorbers are good emitters).

Furthermore, as alluded to earlier, the detection of target contaminant molecules concerns resolving frequencies and strengths of TL absorption by the target contaminant molecules (small radiance) superimposed onto the total liberated emissions field (dominant radiance). Essentially, the process involves: stimulating vibrations of target contaminant molecules with external near IR radiation which are carried onto a dynamic MIR flux liberated by the irradiated material and containing fundamental resonances of target contaminants that become pronounced when the induced thermal gradient of the sample peaks. These vibration bands quench as the gradient diminishes and the surface reaches thermal equilibrium after an increasing time of irradiation. As such, TL is the radiometric carrier of the target contaminant's infrared spectrum (fingerprint) in a finite timeframe of beam irradiation. This thermal gradient period of production collapse is referred to as a window of thermal opportunity for remote sensing ($\Delta \tau$). It is dependant on the physical nature of materials, experimental conditions, and data handling factors including: difference of absorption coefficient between target contaminant and strata, density of target contaminant, incident beam energy and intensity, scan rate/resolution of the radiometer instrument, and several other optical, electronics, and algorithmic signal processing factors.

Modem computational methods of statistical physics are employed to develop model surface temperature gradient building/collapse behavior and TL flux production rate produced by surface irradiation. Temperature gradient, in this sense, is considered a perturbation on the system's ambient state of thermal equilibrium (or quasi equilibrium). One modeling approach for this induced thermal gradient phenomenon is to consider the gradient a small perturbation from ambience and cast the Onsager relationships into a layered boundary value type problem for framing hydrodynamic partial differential equations (PDEs). For example, under this modeling approach the following boundary conditions could apply: $T_a$=constant, and $\delta T/\delta \tau|_{\tau=\tau_{ss}}=0$; where $T_a$ is ambient temperature the instant before irradiation ($\tau$=0), and $\tau_{ss}$ is the time in which thermal equilibrium is attained at elevated steady state temperature of the material during constant beam irradiation. Deriving analytical or numerical solutions of the hydrodynamic PDE with these boundary conditions is the subject of ongoing research, and is expected to reveal some additional useful physical factors governing life cycle of gradient and evolution of TL flux density [$\delta_\tau R(\nu, \tau)$]. Of particular interest is deriving the gradient open-close cycle $\delta_\tau T(\nu, \theta, \pi[s,p]; \tau)$; and quantifying how this affects density of states $\int_{\nu(mir)} \int_{\Delta \tau} \delta_\tau R(\nu, \theta, \pi[s,p]; \tau) d\tau d\nu$; given energy $\nu$, angle of incidence $\theta$, polarization $\pi[s,p]$(s=parallel, p=perpendicular to the surface's statistical normal vector), and duration $\tau$ of the incident beam. A dependence of $\sigma(\nu, \pi[s,p])$ and $\kappa(\nu, \pi[s,p])$, into the model for $\delta_\tau R$ is implicit and may be tested for various material case dependencies, as functions of beam wavelength and polarization, should these parameters have a significant effect on $\delta_\tau R$. Furthermore, the progression of thermal gradient and its relationship with TL flux density may be evaluated by coupling a genetic algorithm (GA) to $\delta_\tau R(\nu, \theta, \pi[s,p], T(\tau); \tau)$ that is made to sample variances of $\nu$, $\theta$ and $\lambda[s,p]$ with irradiation time, bounded by ambient to steady states of thermal equilibrium. These variances, placed on variables of the pump beam, should correspond to the actual operation parameters of a sensor system. Optimization of the GA would then proceed with this goal: maximum temperature gradient for minimum irradiation time. Consequently, a TL instrument will perform best in "real time" when designed around beam and instrument parameters satisfying this GA goal criterion:

An isotopic a $CO_2$ laser (tuned to a fringe P-branch transition wavelength at 12.1 μm, just outside the TL detection bandwidth), or magnetron (W-band microwave emission line at 2.45 GHz) may also be used as sources for pumping TL from terrestrial (sand and soil) and synthetic (asphalt, concrete, painted metal) test samples, before and after a contaminant was applied. For example, experiments have been conducted on surfaces contaminated by the following Chemical Warfare Agent (CWA) simulant liquid compounds: dimethyl methyl phosphonate (DMMP, volatile simulant of the G agents); diethyl methyl phosphonate (DEMP, volatile, another simulant of the G agents); and polydimethy siloxane (SF96, a non-volatile, simulant of the nerve agent VX). Simulants possess similar refractive indices and rheology of the nerve and blister agent organic class, but they do not share the lethally toxic property. A landscape contaminated by exploded ordinance, for instance, was simulated. In this case, the simulant liquid was ejected onto the terrestrial/synthetic test sample by ultrasonic nebulization. Surface density of the deposited aerosol, after settling onto/into the strata, was kept below 5 mg/cm$^2$, a de facto minimum concentration detection capability requirement for a sensor, to be useful for military tactical field deployment.

It became clear from these studies that criteria for successful detection exist; namely, streaming interferogram outputs by the TL measuring instrument—a Michelson interferometer—must be synchronized and balanced to the power and duration of an irradiating beam pumping TL. Specifically, sensing a spectral signature emergence of target contaminant in $\delta S_n(\nu_{mir},\tau)$ required proper calibration of the combined optic (irradiating beam), electronic (interferometer drivers and data acquisition), and algorithmic (interferogram preprocessing) subsystems of the sensor. For example, SF96 on soil was revealed by 12.1 μm beam wavelength and 0.7 W/cm$^2$ irradiation, 4 Hz interferometer scan rate, 20 co-added and averaged interferometer data sets per spectrum, and 40 s irradiation period (first onset of thermal bands).

The isotopic $CO_2$ laser and magnetron sourced TL sensor systems of the research described above posed several problems, however, if the technology were to be advanced and deployed in the open environment for in situ field usage. In the case of laser irradiation, a CaF filter was placed at the entrance aperture of the interferometer for blocking the 12.1 μm scattered light. Unfortunately, this filter also attenuates useful TL detection bandwidth. Moreover, the $CO_2$ laser beam is not a practical source for area heating (a requirement for tactical sensing), unless a spatial scanning is incorporated into the sensor design. Leakage/exposure from the reflected/scattered pump beam is a safety issue regarding the latter case of microwave heating and TL stimulation. Complete shielding of this source, starting at the magnetron horn, is challenging and costly given that personnel must have absolute protection in a high power field sensor unit. Because of these optical and operational concerns, incoherent NIR sources, which generally are less prone to causing eye and body tissue damage, were explored. As such, a TL sensing system using halogen lamp transmitters integrated into a substantially identical scanning interferometer/spectrometer receiver unit, was investigated to determine whether it would be useful for surface contamination detection.

The NIR source in the preferred embodiment is based on commercially available and relatively inexpensive halogen lamp technology in which a tungsten (W) filament and trace bromine gas ($Br_2$) are encapsulated in a quartz bulb. The lamps operate as follows: (1) W atoms evaporate when the filament attains 3050 degrees C., and migrate then deposit onto the bulb's inner wall surface; (2) W and Brz bond at this surface upon the quartz reaching 2500 degrees C., freeing the W residue built up on that wall after its migration from filament; (3) the bonded $WBr_2$ gas molecules migrate back toward the hot W filament and dissociate. This cycle continues ad fin provided filament and wall temperatures are maintained. The bonding and dissociation of $WBr_2$ gives the halogen lamp its characteristic NIR emission profile: peak intensity at about 1.10 μm and decreasing to near zero intensity at 4.57 μm. These lamps also possess some bandwidth in the ultraviolet through visible, but minor or nil bandwidth in the middle infrared TL band. Other similar near infrared sources may likewise be employed in alternative embodiments.

A laboratory embodiment of a TL device according to the present invention is shown in FIG. 1. A surface irradiation source 100 (shown in more detail in inset FIG. 7) includes 8 ring mounted Gilway model L523 G halogen lamps 102 with gold plated parabolic reflectors for collimation of beams 104, and filter discs 106 for blocking 600-1500 cm$^{-1}$ TL bandwidth. The superimposed beams are centered on axis of the ring mount, 60 degree tilt angle, 11.7 cm. beam travel, 28 cm$^2$ beam spot size, 75 W maximum output power at 12 Volts, 1.100 μm (near infrared) peak emission output per lamp with wide spread.

A 90 degree flat mirror reflector 130 reflects radiation to a MIDAC model M2401 interferometer 140. Interferometer 140 performs 4 interferograms/s scan rate, 3.8 cm. clear aperture, 20 mrad FOV, and operating under the Spectral-Calc Version 2.2 software package, Galactic Industries, 1991.

As shown in FIG. 7, beam source 100 includes a system of 8 NIR lamps 102, equally spaced around a ring shaped fixture 110 for pumping TL flux $\delta_\tau R(\nu_{mir},\tau)$ as described above. The bulb of each lamp 102 is positioned on a foci of a gold coated parabolic reflector 104 for collimation of emissions output (the reflected beam actually has a 14 degree divergent beam angle). Maximum power output per lamp is nominally 75 W. Each lamp 102 is tilted 61 degrees on axis and displaced approximately 12 cm from the center of sample terrestrial surface 120, producing an area of illumination (brightest spot size) of approximately 28 cm$^2$. To protect against any possible MIR leakage (either directly from a bulb 102, or from the Au surface of any heated parabolic reflectors 104), 2 mm thick optical filter disks 106 are mounted in front of each reflector 104. Filters 106 pass better than 80% NIR emissions having peak intensity at about 1.10 μm and decreasing to near zero intensity at 4.57 μm, and completely null all TL bandwidth (6.67-16.67 μm). Although a number of different lamps may be used, lamps 102 were obtained from the Gilway Technical Lamp Company, Woburn, Mass., unit model L523 G and wired in parallel to a Hewlett Packard HP B Series 6652A programmable 0-20 VDC power supply. Barr Associates, Inc., Westford, Mass., fabricated filters 106 (model ITO 2.0).

While a continuous NIR pump beam source 100 is preferred for its simplicity and ability to heat large areas of sample in a relatively safe radiological manner, in alternative embodiments of the present invention, spectral interference can likewise be avoided by using pulsed beam stimulation inside the TL bandwidth, and gating measurements during off beam dwell times.

Test sample 120 is soil that was gathered from the Dugway Proving Ground, Utah. While Dugway soil is a de facto standard for surface contaminant tests the detection techniques according to embodiments of the present invention would work equally well on other soils and surfaces. The soil fills a petri dish elevated vertically into position where 8 superimposed (slightly divergent) beams from beam source 100 centrally illuminate the sample over an area of approximately 28 cm$^2$, with beam intensity of 0.92 W/cm$^2$. Measurements from this sample were conducted in situ, and when a spray of 0.66 ml of SF96 50 was applied across the irradiated area (or wider). Surface density of target contaminant was kept below 5 mg/cm, another de facto rule of thumb specification regarding military remote sensing.

SF96 50 is a polymer and derivative of polydimethyl siloxane, a nonhazardous viscous oil with optical properties and rheology similar to that of the chemical nerve agent Ethyl S (2Diisopropylaminoethyl) Methylphosphonothiolate or VX The General Electric (GE) Company, Silicone Products Division, manufactures it. According to GE's material safety data sheet, SF9650 is an odorless, clear, insoluble (in water) liquid with boiling and flashpoint>204 C (i.e., nonvolatile to the NIR beams of this intensity). Other properties include 0.97 specific gravity and 0.959 gm/cm$^3$ mass density. It is commonly used as an engine lubricant.

A flat IR mirror 130 directs heated surface emissions by the soil to an infrared spectrometer 140. The spectrometer 140 measures TL flux density throughput [$\delta_\tau RR(\nu,\tau)$] interferometrically, from which the difference-spectra metric $\delta S_n(\nu_{mir},\tau)$ of sample is computed. Spectrometer 140 is preferably a scanning Michelson interferometer system. In the embodiment illustrated, spectrometer 140 includes a ZnSe window and beam splitter optics, a 2.54 cm diameter limiting aperture, and 90 degree parabolic mirror for focusing collimated throughput onto a 1 mm$^2$ HgCdTe photoconductive chip, cooled to liquid nitrogen temperature (77 degrees K). It is a product of the Midac Corporation, Costa Mesa, Calif., Model 2401 C. Data acquisition and control software called SpectrCalc, Galactic Industries, Inc., controls the instrument via menu driven scripts run in a Microsoft DOS environment.

A raw database of stored interferograms from an experimental run is imported into a Graphic Relational Array Management System software tool (GRAMS32, a product of Thermo Galactic, Salem N.H.) for preprocessing of interferograms (averaging, grouping) spectral conversion (Fourier transformation), subtraction, and graphical display. The resultant $\delta S_n(\nu_{mir},\tau)$ data fields are then imported into the Interactive Data Language program (IDL, a product of Research Systems, Incorporated), version 7.0, for surface and contour imaging of data, and other visualization tasks.

In general, a modern, general purpose personal computer will provide a suitable platform to perform data processing, signal processing and control functions according to the present invention. Such a computer or processor may be, or may include, one or more general or special-purpose microprocessors, digital signal processors (DSPs), application specific integrated circuits (ASICs), programmable logic devices (PLDs), field programmable gate arrays (FPGAs), or other appropriate devices or combination of such devices. In some embodiments, a processor may be integrated with dedicated image acquisition hardware, firmware and software. A processor may also include devices appropriate for buffering, amplification, and signal conditioning. A variety of general-purpose programming languages, together with standard numerical methods, signal processing and data analysis routines may be used to implement embodiments of the present invention. High level programming and application development platforms may also be used. As will be recognized by those skilled in the art, parallel processing techniques may be used to advantage in some embodiments of the present invention.

The experiment began upon the simultaneous switching on of beam source 100 and spectrometer 140. A gain of 4 from the interferometer's electronic digitization circuit yields near full dynamic range in that instrument. We applied triangular apodization of interferograms for filtering its centerburst amplitudes (which contains no TL spectral information). The interferometer has a fixed 4 Hz (interferograms/s) scan rate, which is dictated by an oscillating mirror component and laser synchronization/digitation servomechanism. Interferograms were grouped, coadded, averaged, and Fourier transformed in serial order of increasing irradiation time $\tau$, with constant beam intensity.

The grouped quantities of interferogram coadditions divided by scan rate of instrument equals elapsed $\tau$ for per spectrum computation (Fourier transformation). These spectra are subtracted in contiguous order, compiled, and stored as $\delta S_n(\nu_{mir},\tau)$ where bandwidth $\nu_{mir}$ spans $500 \leq \nu_{mir} \leq 1600$ cm$^{-1}$ and corresponds roughly to a 60% spectral responsivity by the spectrometer. This $\nu_{mir}$ region is the fingerprint spectrum zone for Chemical Warfare Agent (CWA) and simulant compounds, and most organics in the phosphonated organic class of which the CWAs are members.

Although the results shown here reference the specific case of detecting SF96 sprayed on soil, such details are intended to be instructive rather than restrictive. It will be appreciated that many variations may be made in surface material (i.e., inhomogenuous dielectrics), target contaminants (most organics that possess at least one strong vibration resonance band inside the TL region) and sensor design/operation without departing from the scope of the detection method in embodiments according to the present invention.

Figure 2:
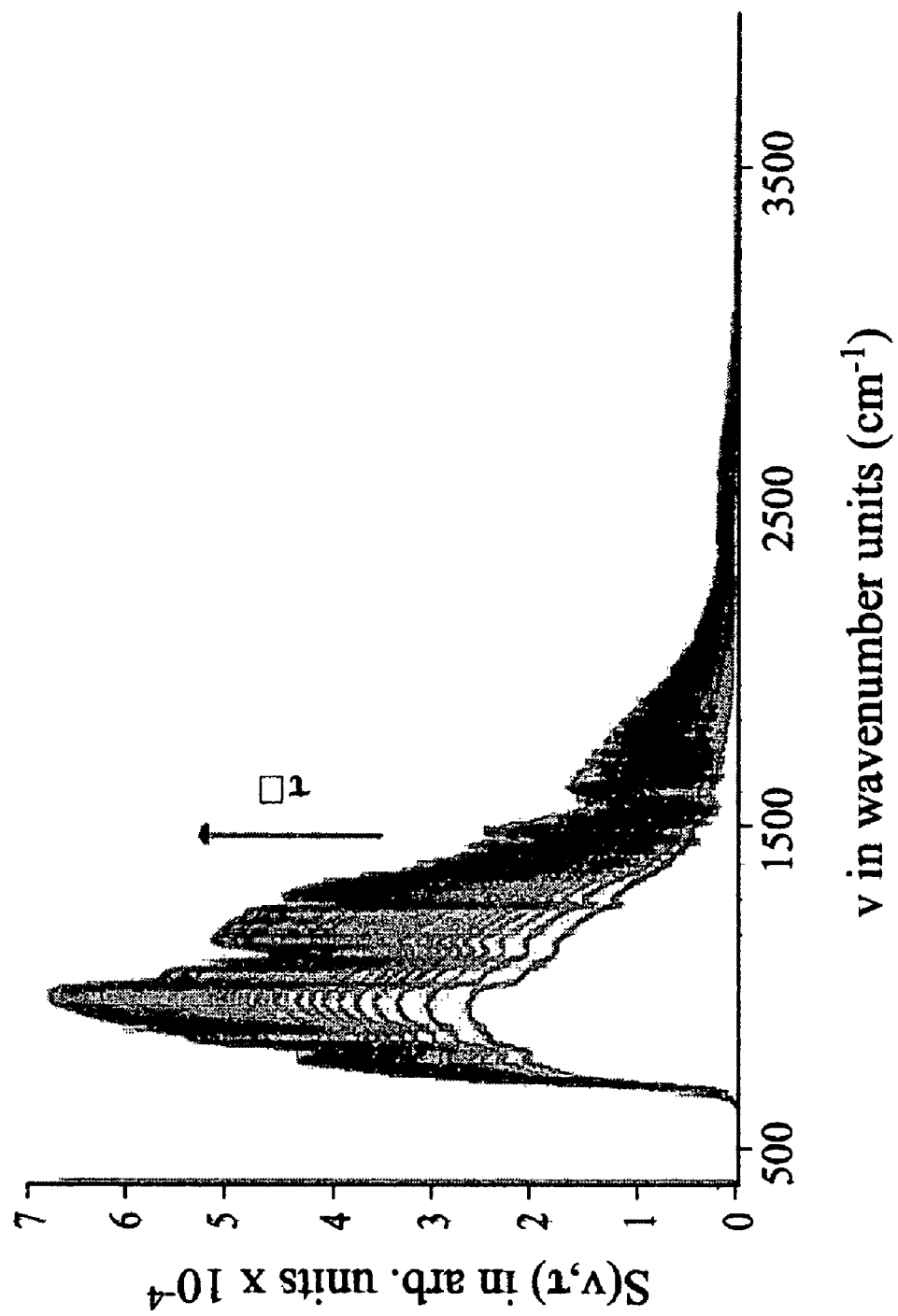
FIG. 2 shows a diagram of unscaled emission amplitudes liberated by Dugway Proving Ground soil during beam irradiation as measured by the sensor system of FIG. 1.

FIG. 2 is a graphical display of spectra per the soil sample of FIG. 1, and measurement techniques explained above. These data, and all data that follow, are raw in the sense that no statistical manipulations or filtering were performed. The soil is uncontaminated, in its natural state, and measurement parameters include: 0.925 W/cm$^2$ beam intensity and 295 s total time of irradiation; 4 Hz (interferograms/s) scan rate, gain=4, and 2 cm$^{-1}$ resolution of spectra. Parameters, of measurement also include: triangular apodization of interferograms; 20 coadded then averaged interferograms per spectrum at 2 cm$^{-1}$ resolution; Interval Of Validity (IOV) is the MIR region of $500 \leq \nu_{mir} \leq 1600$ cm$^{-1}$ (wavenumbers), or $6.3 \leq \nu_{mir} \leq 20.0$ μm (micrometers).

A monotonically increasing emissions envelope and (not so obvious, in this energy scale) shifting of this envelope toward higher energies represents heating of the sample, i.e., until thermal equilibrium is attained with time of irradiation $\tau$. A quantification of this heating rate can be determined by tracking amplitude and energy [frequency] of the major emissions peak of FIG. 2 as a function of $\tau$. These spectra have cutoff margins due to transmission of infrared radiance through the interferometer's ZnSe window, beam splitter optic, and via the responsivity of the HgCdTe photoconductive element where MIR throughput is focused. (This cutoff bandwidth is well beyond the $500 \leq \nu_{mir} \leq 1600$ cm$^{-1}$ region, and does not hinder TL detection performance.) As expected, FIG. 2 portrays a rapid heating rate (increased emission amplitudes and spectra shift) by the sample immediately upon beam exposure, and the convergence of these changing spectra toward steady state (thermal equilibrium).

Figure 3:
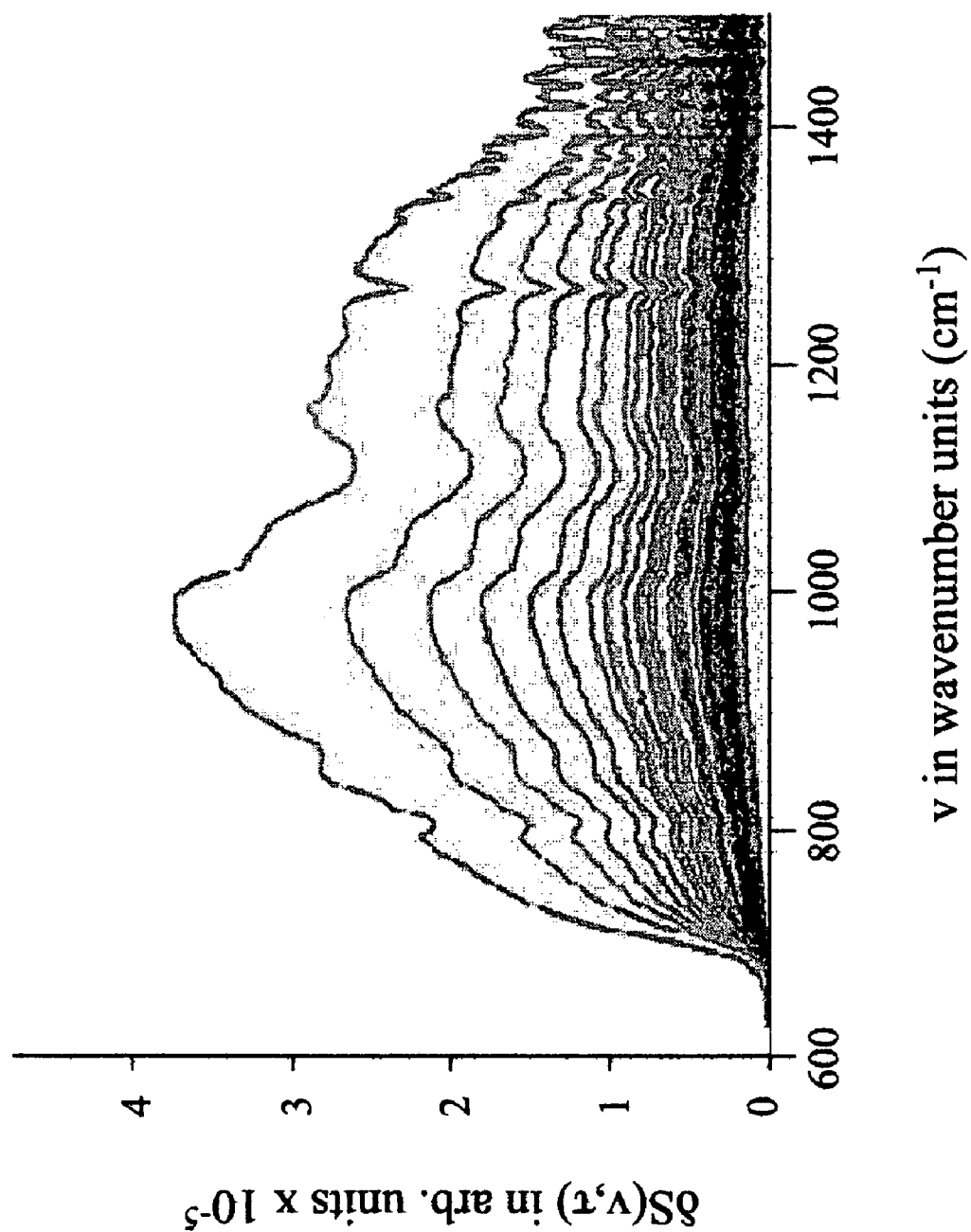
FIG. 3 shows a diagram of the raw subtraction of contiguous spectra from FIG. 2 for dry, in situ, Dugway soil inside the 600-1500 cm$^{-1}$ TL detection region.

FIG. 3 shows the affined sets of subtracted adjacent spectra of FIG. 2: $\delta S_n(\nu_{mir},\tau)=\{S(\nu_{mir},\tau_{n+1})-S(\nu_{mir},\tau_n)\}$, from $[\tau_a, \tau_b]$, where the subscript a is the time where beam source 100 was switched on and b is 295 s. The transient time interval per spectrum is: N/SR+ϵ(5 s); where SR is interferometer scan rate, N is the number of interferogram coadditions, and ϵ is a small FFT computation time (ϵ,=0 if spectral conversions are not done on the fly). The raw difference-spectra presented in FIG. 3 show fine absorption detail in the sharp bands beyond 1250 cm$^{-1}$, and broad residual emissions called Reststrahlen. (Reststrahlen emissions by silicates and minerals with silica content, are abundant in the infrared.) These absorption and emission phenomena are manifestations of the organic and mineral compositions of this particular soil sample, and are most prevalent early on during irradiation τ, where the spectra of FIG. 2 are most separated.

Figure 4:
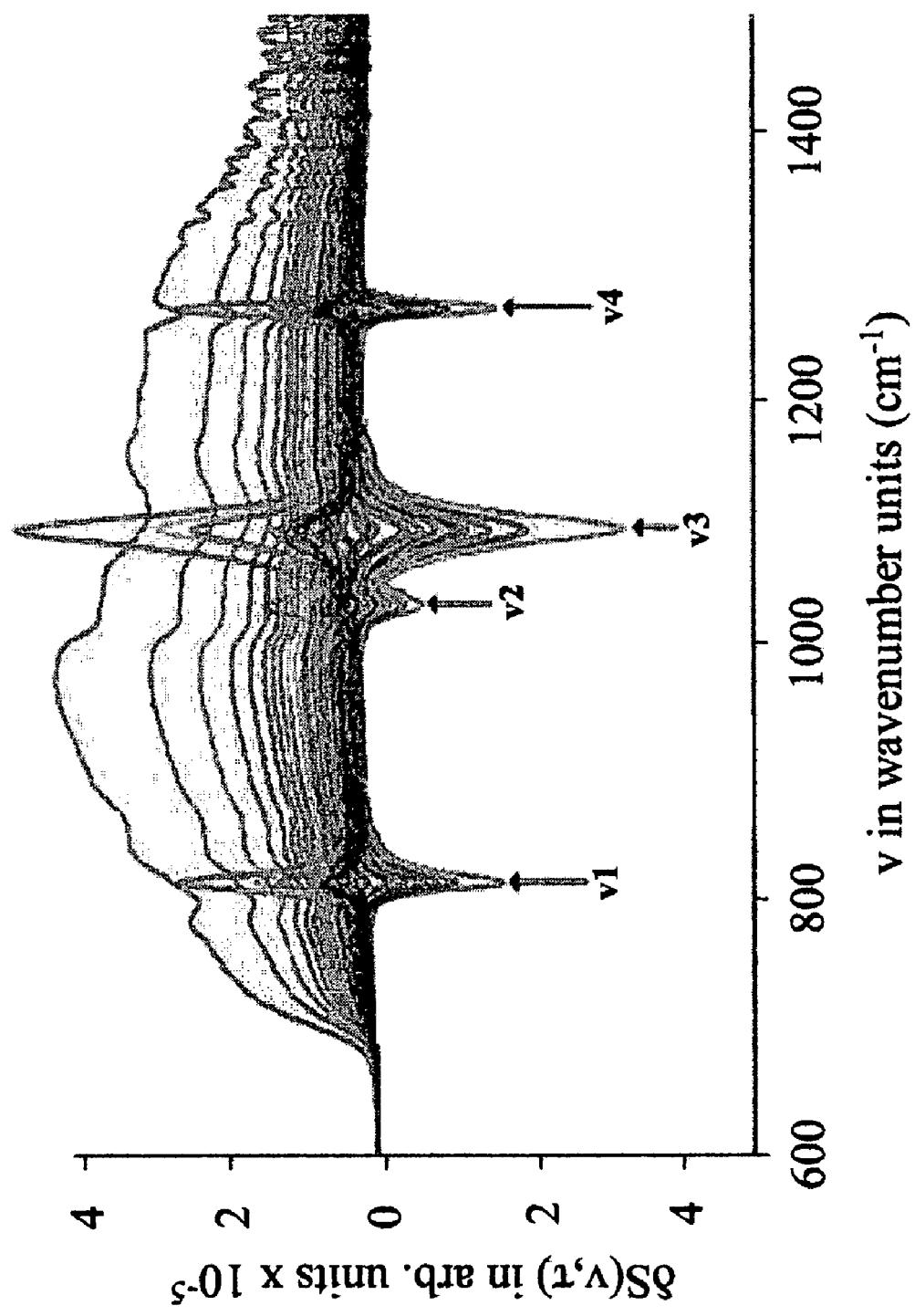
FIG. 4 shows a diagram of the raw subtraction of contiguous spectra for the soil sample of FIG. 3 after light spray (approximately 5 mg/cm$^2$) of SF96 (a simulant of the chemical nerve agent VX).

FIG. 4 is the same measurement as in FIG. 3, except now the soil is sprayed with a nerve agent simulant compound. The target contaminant, SF96-50, is an oily silicone polymer compound [—Si(CH$_3$)$_2$O—]$_n$ exhibiting these excitable, fundamental, molecular vibration states: $\nu_1$,=816.4 cm$^{-1}$, a S$_1$—CH$_3$ rocking normal mode; $\nu_2$=1035.8 cm$^{-1}$, a Si—O—Si stretching normal mode; $\nu_3$=1092.8 cm$^{-1}$, another Si—O—Si stretching normal mode; and $\nu_4$=1267.0 cm$^{-1}$, a Si—CH$_3$ symmetrical stretching normal mode. Polarity reversal behavior of the molecular resonance bands may also be indicative of target contaminant presence.

FIGS. 3 and 4 illustrate the highly effective nature of an embodiment of a method of detection according to the present invention. Contaminated and dry soil data correlate precisely early on in τ by inspection of the respective $\delta S_n(\nu,\tau)$ measurements. As shown in FIG. 4, the first evidence of target contaminant presence arises after about 132 s of NIR beam heating, when the SF96 fingerprint bands first emerge. They subsequently strengthen and then collapse in τ with a behavior of polarity reversals. This universal band polarity pattern (all bands of the target contaminant flip in unison) is precisely what was expected based on our past coherent laser and magnetron beam stimulation experiments. The beam duration in which this behavior occurs corresponds precisely to the window of thermal opportunity. Further study of the statistical physics framework will likely provide additional bases for explaining this dynamic behavior.

Figure 5:
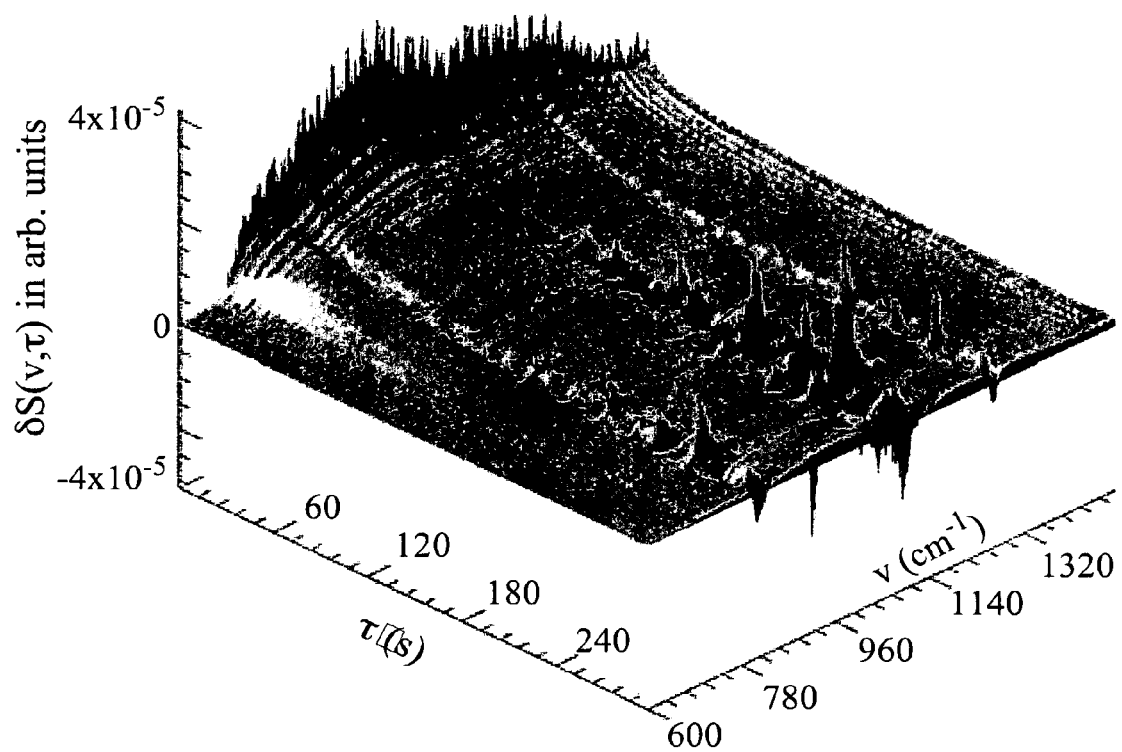
FIG. 5 shows the difference spectra metric (FIG. 4) extended along the beam irradiation τ.

The surface of FIG. 5 is the data of FIG. 4 extended along the beam irradiation time dimension τ. Opening of the thermal detection window occurs approximately when τ=132 s. Swings in polarity of the fundamental molecular vibration band amplitudes by the target contaminant (after opening of window) are manifestation of the thermal nonequilibrium state of a sample. This behavior diminishes and the bands disappear as steady state temperature is attained in τ.

Figure 6:
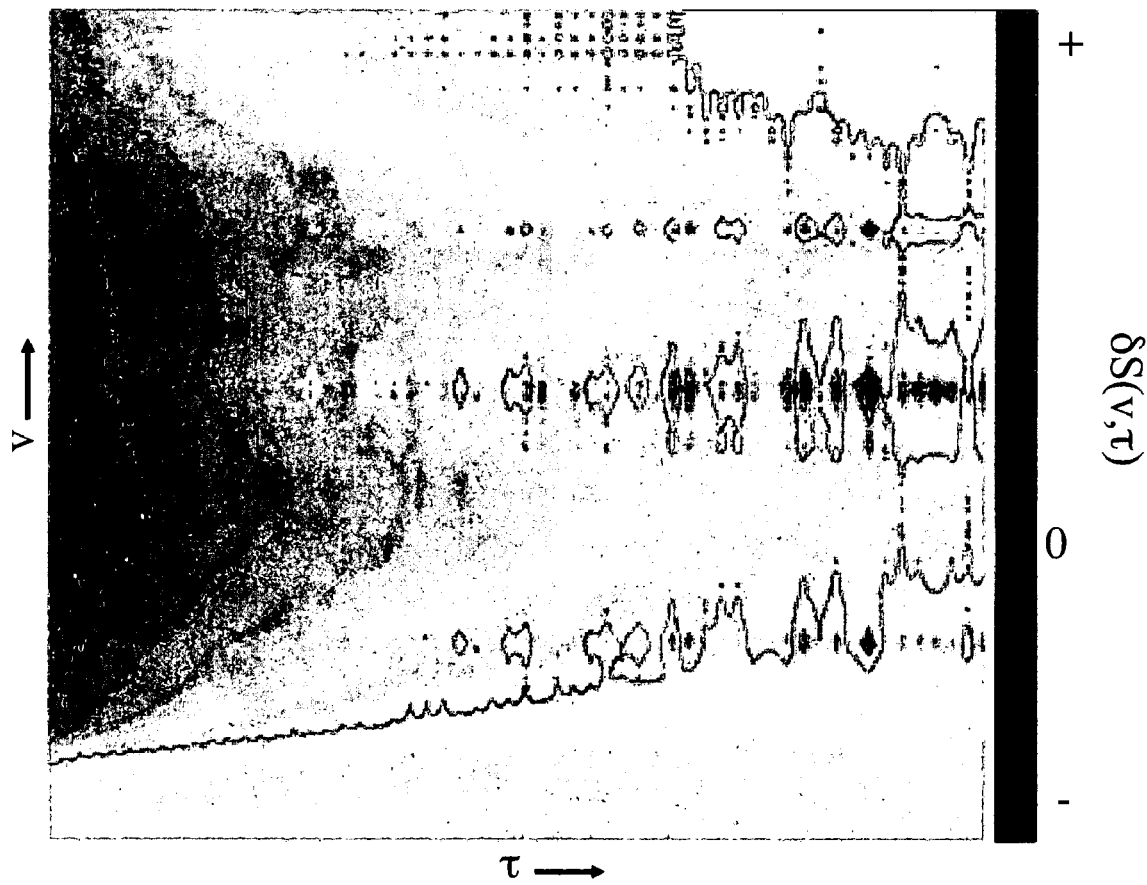
FIG. 6 shows a digital contour image perspective of the raw difference-spectra metric for contaminated soil (FIG. 3) to provide greater insight into the thermal behavior of the target contaminant signature bands.
Figure 7:
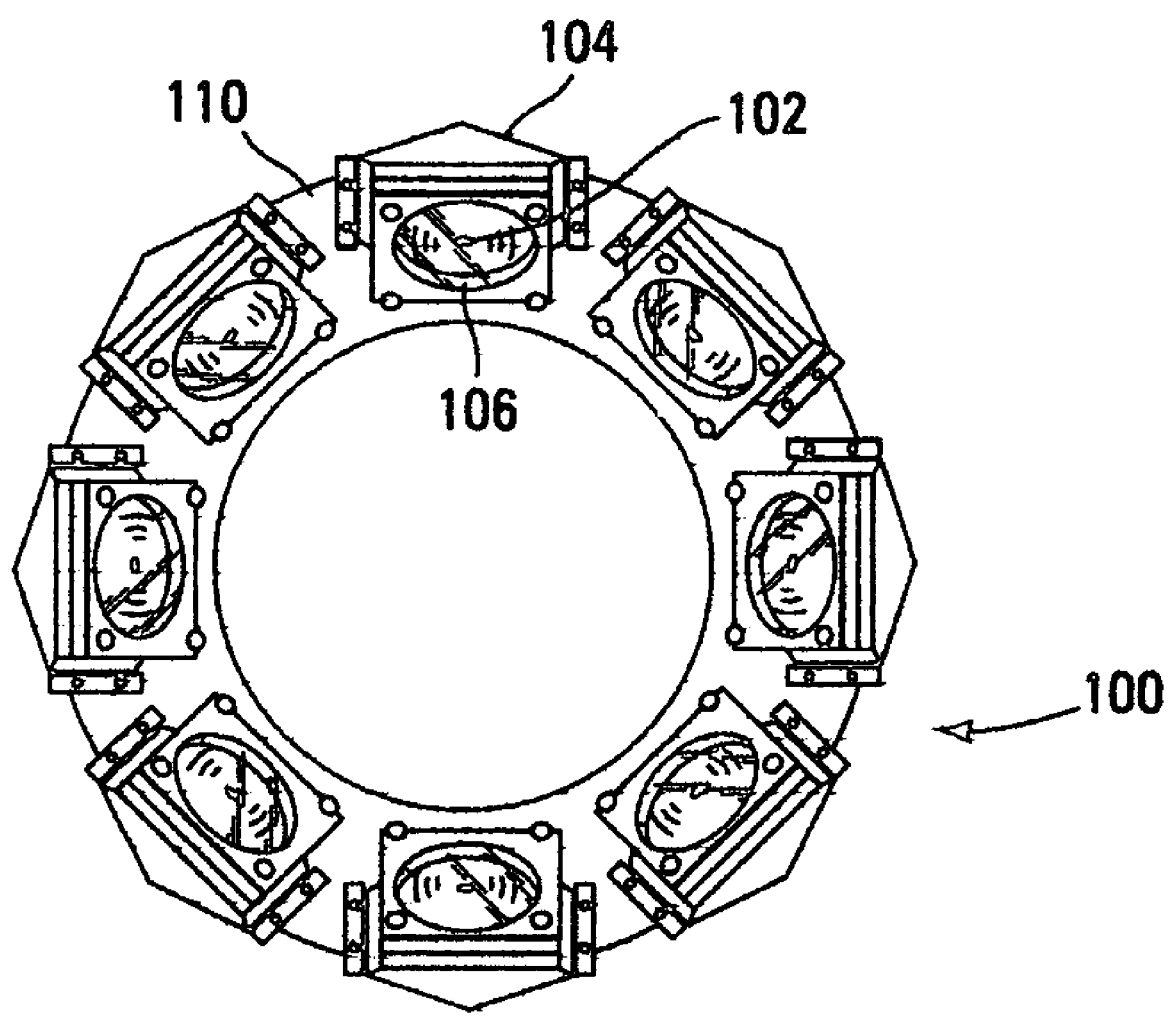
FIG. 7 shows a diagram of an NIR Beam source constructed from a ring of 8 halogen NIR lamps in parabolic reflectors.

FIG. 6 is a digital contour image of the surface of FIG. 5 along the ν-τ plane. Surface and image graphics are produced in IDL from the raw 27144 ASCI datum of FIG. 4, and these plotting parameters: 3 fields, long, integers; τ axis ϵ[10.0, 295.0] s, ν axis ϵ[600.0, 295.0] cm$^{-1}$, $\delta S(\nu, \tau)$ axis ϵ[3.29, 4.72]×10$^{-5}$ arbitrary units; τ and ν axes dimension=250. The perspectives of data shown in FIGS. 5 and 6 are illustrative of the heating of irradiated soil and its consequential TL thermodynamics. They can be quite usefully applied toward structuring time series algorithms that perform pattern recognition band location, amplitudes, and polarity of a target contaminant. These characteristics of pattern and behavior are the information needed to train, test, and validate classification and/or prediction neural network systems. Implementation of optimum neural networks into the sensor system will establish a most useful real-time surface contamination detection capability.

CONCLUSION

Embodiments of TL spectroscopy systems and methods for remote sensing and detection of surface chemical contamination according to the present invention provide significant improvements over existing stand-off target contaminant detection systems and are capable of achieving great detection accuracy over a broad range of chemical target contaminants in a relatively short time frame with reduced radiological risk. A near IR beam source, such as a halogen lamp based source with peak intensity at about 1.10 μm and decreasing to near zero intensity at 4.57 μm beam bandwidth, irradiated contaminated soil and was successful in stimulating the target contaminant's middle infrared signature spectrum in liberated thermal emissions, with good signal to noise (S/N) ratio, thereby allowing for its remote identification by means of a difference-spectra metric of this liberated thermal luminescence. In one example, the chemical warfare agent simulant SF96 was detected in this manner at 5 mg/cm$^2$ surface density and less, after 132 seconds of 0.925 W/cm$^2$ beam exposure without a need for statistical handling of data. This is compared to 40 s at 0.7 W/cm$^2$ via 12.1 μm CO$_2$ laser beam irradiation. In contrast to CO$_2$ laser sources and the like, NIR lamp illumination has the ability to heat large areas of sample in a relatively safe radiological manner.

It will be clear to those of skill in the art that the above embodiments may be altered in many ways without departing from the scope of the invention. For example, while a halogen lamp based source has been specifically described, other similar NIR beam sources may be employed in alternative embodiments. In other alternative embodiments, pulsed or gated coherent beam sources in the MIR band may be used. In addition, while neural networks have been specifically described in connection with optimization of target contaminant model difference-spectra, a wide variety of optimization routines may be employed in one or more alternative embodiments. Accordingly, the scope of the invention should be determined by the following claims and their legal equivalents.

It is anticipated that a number of additional techniques, refinements, and additions to the system may be employed to further improve S/N of the target contaminant's thermal spectrum, reduce irradiation timeframe for the emergence of spectrum signature by the target contaminant, and obtain shorter detection onset periods. Such additions and substitutions are also within the scope of the invention. Examples include but are not limited to optical (notch) filtration of the broad NIR beam may to reduce Reststrahlen emissions; polarization selectivity of irradiating beam may provide for better absorption; increased interferometer scan rate and improved alignment to improve S/N. As neural network pattern recognition and related optimization systems improve, it may also be possible to extract the weak signature bands earlier in the beam irradiation timeframe.

What is claimed is:

1. A system for remote sensing and detection of chemical target contaminants at a surface, comprising:
   (a) a near infrared irradiation source that includes:
      a plurality of near infrared lamps mounted on and substantially equally spaced around a ring shaped fixture, each of said lamps including a parabolic reflector, wherein source emission from each lamp is generated by a halogen lamp that is positioned on foci of its reflector thereby collimating the emission beam of each lamp; and a plurality of optical filters equal in number to said lamps, each filter mounted in front of a corresponding reflector to exclude middle infrared emissions, and wherein the filtered beams from said lamps are projected and superimposed onto irradiated sample located at a fixed distance normal to the central axis of said ring shaped fixture;

(b) an infrared mirror to direct thermal luminescence from the irradiated sample;

(c) a Fourier transform infrared spectrometer to receive and process the thermal luminescence from the infrared mirror into thermal luminescence data; and (d) a Michelson interferometer to produce interferograms from the thermal luminescence data.

2. The system of claim 1, wherein the interferograms are co-added in sets, Fourier transformed in contiguous sets to produce spectra and spectra are subtracted to form detection-spectra metrics of the thermal luminescence.

3. The system of claim 2, wherein the detection-spectra metrics is input to a neural network pattern recognition system for detection of target contaminant signature spectra collecting data.

4. The system of claim 2, wherein the system provides substantially real time detection and identification of target contaminants and further comprises an alarm to warn of the presence of target contaminants.

5. The system of claim 4, wherein the system provides a warning of the presence of target contaminants if target contaminant bands emerge in said difference spectra metric of thermal luminescence.

6. The system of claim 5, wherein target contaminant bands exhibit a polarity reversal behavior in the thermal luminescence difference spectra detection metric.

7. The system of claim 6, wherein the irradiation source and spectrometer are synchronized to collect data in the thermal detection window.

8. The system of claim 1, wherein the near infrared radiation source and Fourier transform infrared spectrometer are substantially synchronized while collecting data.

9. The system of claim 1, wherein the near infrared radiation source emits radiation substantially in a near infrared band of peak intensity at about 1.100 µm and decreases to zero intensity at about 4.57 µm.

10. The system of claim 1, wherein power of the near infrared radiation source is continuous wave for continuous data collection or pulsed for data collection only during off beam dwell time.

11. The system of claim 1, wherein thermal luminescence data is processed over a thermal detection window in which a temperature gradient on the irradiated surface reaches a maximum.

12. The system of claim 1, wherein a neural network performs pattern recognition on said thermal luminescence spectra.

13. The system of claim 1, further comprising means to operate the irradiation source in continuous or pulsed modes to generate thermal luminescence from an irradiated surface.

14. The system of claim 1, wherein said plurality of near infrared lamps comprises eight near infrared lamps.

15. A method for detecting target contaminants, comprising:

irradiating a surface with a near infrared energy source to induce a thermal gradient, said near infrared energy source comprising a plurality of near infrared lamps mounted on and substantially equally spaced around a ring shaped fixture, each of said lamps including a parabolic reflector, wherein source emission from each lamp is generated by a halogen lamp that is positioned on foci of its reflector thereby collimating the emission beam of each lamp; and a plurality of optical filters equal in number to said lamps, each filter mounted in front of a corresponding reflector to exclude middle infrared emissions; and wherein the filtered beams from said lamps are projected and superimposed onto irradiated sample located at a fixed distance normal to the central axis of said ring shaped fixture;

scanning the surface interferometrically to detect middle-infrared emissions;

windowing detected middle infrared emissions to capture data substantially centered on a thermal gradient peak;

processing the data to extract molecular vibration bands; and identifying target contaminants by employing said molecular vibration bands.

16. The method of claim 15, wherein identifying target contaminants by employing said molecular vibration bands comprises employing a neural network model trained against known molecular absorption frequencies of target contaminants.

17. The method of claim 16, wherein a minimum near infrared energy source irradiation time $[0, \tau_{min}]$ to maximize thermal luminescent flux as the surface is driven into thermal non-equilibrium is estimated by performing a numerical optimization on one or more irradiating source parameters.

18. The method of claim 17, wherein the optimization comprises a genetic algorithm that operates on the one or more irradiating source parameters in order to arrive at a thermally dynamic state of the surface in minimum T, i.e., $\partial^2 \mathcal{R}/\partial \tau^2|_{\tau=min}=0$.

19. A method for detecting a target contaminant, comprising:

irradiating a surface with a source of near infrared energy to produce a thermal gradient, said near infrared energy source comprising a plurality of near infrared lamps mounted on and substantially equally spaced around a ring shaped fixture, each of said lamps including a parabolic reflector, wherein source emission from each lamp is generated by a halogen lamp that is positioned on foci of its reflector thereby collimating the emission beam of each lamp; and a plurality of optical filters equal in number to said lamps, each filter mounted in front of a corresponding reflector to exclude middle infrared emissions; and wherein the filtered beams from said lamps are projected and superimposed onto irradiated sample located at a fixed distance normal to the central axis of said ring shaped fixture;

gathering middle infrared emissions liberated from the surface during a window centered on maximum thermal gradient produced by the irradiation;

scanning the windowed middle infrared emissions interferometrically to produce interferograms;

Fourier transforming the interferograms into spectra;

sequentially subtracting the spectra in the window to arrive at difference spectra; and processing the difference-spectra to identify a target contaminant.

* * * * *